(12) United States Patent
Perlmutter et al.

(10) Patent No.: US 7,012,142 B2
(45) Date of Patent: Mar. 14, 2006

(54) PROCESS FOR PREPARATION OF BICYCLIC AND POLYCYCLIC MOLECULES

(75) Inventors: Patrick Perlmutter, Elsternwick (AU); Mark Rose, Seddon (AU); Neeranat Thienthong, Heidelberg (AU)

(73) Assignee: Monash University, Victoria (AU)

( * ) Notice: Subject to any disclaimer, the term of this patent is extended or adjusted under 35 U.S.C. 154(b) by 146 days.

(21) Appl. No.: 10/423,563

(22) Filed: Apr. 25, 2003

(65) Prior Publication Data

US 2004/0010140 A1 Jan. 15, 2004

Related U.S. Application Data

(63) Continuation of application No. PCT/AU01/01379, filed on Oct. 26, 2001.

(30) Foreign Application Priority Data

Oct. 27, 2000 (AU) .............................................. PR1057

(51) Int. Cl.
*C07D 451/02* (2006.01)
*C07D 491/00* (2006.01)

(52) U.S. Cl. ........................... 546/90; 546/91; 546/127; 546/131

(58) Field of Classification Search ................... 546/90, 546/91, 127, 131
See application file for complete search history.

(56) References Cited

FOREIGN PATENT DOCUMENTS

| WO | WO 97/40859 | 11/1997 |
|---|---|---|
| WO | WO 99/02526 | 1/1999 |

OTHER PUBLICATIONS

Iida, Hideo, et al.; "A New Synthetic Route to Tropane Alkaloids Based on [4+2] Nitroso Cycloaddition to 1,3-Cycloheptadienes"; *J. Org. Chem.*; vol. 50, pp. 1818–1825; (1985).

Molander, G.A., et al., "Sequenced Reactions with Samarium (II) Iodide. Intermolecular Ketyl–Olefin Coupling/Intramolecular Nucleophilic Acyl Substitution for the Preparation of Six-, Seven-, and Eight-Membered Carbocycles.", *Tetrahedron*, 54, 9289–9302, (1998).

A. Kozikowski, et al., "Synthesis of 8–Oxa Analogues of Norcocaine Endowed with Interesting Cocaine–like Activity", *Bioorganic & Medicinal Chemistry Letters*, vol. 9, pp. 1831–1836 (1999).

P.C. Meltzer et al., "Bicyclo [3.2.1] Octanes: Synthesis and Inhibition of Binding at the Dopamine and Serotonin Transporters", *Bioorganic & Medicinal Chemistry Letters*, vol. 9, pp. 857–862, (1999).

P.C. Meltzer et al., "Structure Activity Relationships of Inhibition of the Dopamine Transporter by 3–Arylbicyclo [3.2.1] Octanes", *Medicinal Chemistry Research*, vol. 8, No. 1/2 pp. 12–34 (1998).

I. P. Kovalev et al., "Catalytic Codimerization of α, β– with γ, σ–Unsaturated Ketones: Novel Stereoselective Method of the Synthesis of Functionalized 8–Oxabicyclo [3.2.1] octanes", *Tetrahedron Letters*, vol. 33, No. 13, pp. 1791–1794, (1992).

K. G. Bowers, et al., "Thromboxane $A_2$ Analogues from 8–Oxabicyclo[3.2.1]oct–6–en–3–ones", *J. Chem. Soc. Perkin Trans.I*, pp. 1657–1666, (1987).

P. Brownbridge et al., "A Simple Route to the 8–Oxabicyclo [3.2.1] Octyl and 9–Oxabicyclo [3.3.1] Nonyl Systems. Synthesis of the 8–Oxa Analog of Cocaine", *Tetrahedron Letters*, No. 46, pp. 4437–4440, (1979).

*Primary Examiner*—Elli Peselev
(74) *Attorney, Agent, or Firm*—Scully, Scott, Murphy & Presser

(57) ABSTRACT

The present application is directed to a method of synthesis of a bicyclic or polycyclic compound of formula I or formula II:

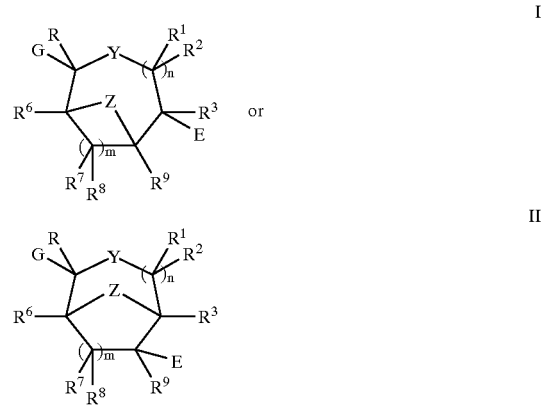

in which E, G, Y, n, m, R, $R^1$, $R^2$, $R^3$, $R^6$, $R^7$, $R^8$ and $R^9$ are as defined.

23 Claims, No Drawings

PROCESS FOR PREPARATION OF BICYCLIC AND POLYCYCLIC MOLECULES

CROSS-REFERENCE TO RELATED APPLICATION

The present application is a continuation of PCT/AU01/01379, filed Oct. 26, 2001.

This invention relates to methods for the synthesis of bicyclic and polycyclic molecules. In particular the invention relates to the use of a sequence of nucleophilic addition followed by one or more ring closures in the synthesis of cyclic molecules, including monocyclic, bicyclic and polycyclic molecules. The methods of the invention are useful in the synthesis of candidate pharmaceutical agents or intermediates in drug synthesis.

BACKGROUND OF THE INVENTION

Cyclic structures are found in many important bioactive molecules, particularly alkaloids such as the tropane alkaloids, which include cocaine and its derivatives, other alkaloids such as opiates, and several classes of antibiotics. They also show great potential in other areas such as conformationally-restricted cyclic amino acids and peptides, and monosaccharides and oligosaccharides, including such molecules which are substituted with amino or other groups, and squalestatin analogues.

It is evident, therefore, that these cyclic structures, such as bicyclic and polycyclic structures, are of great importance from a medicinal point of view. Although there are many reports on the synthesis of selected examples of bicyclic and polycyclic molecules, none of these offers a general solution to the problem of synthesis of all these structural classes. There is, therefore, a great need in the art for a new general process to enable the synthesis of these compounds.

We have now developed a general approach for the synthesis of highly functionalised cyclic molecules, which involves the use of a sequence of nucleophilic addition followed by one or more ring closures ("NARC") to construct a wide variety of enantiomerically pure cyclic compounds. These include mono-, bi- and polycyclic carbocycles, oxacycles, azacycles and thiacycles of varying, but well-defined, size, substitution pattern and stereochemistry. These compounds can be used directly or as intermediates for further syntheses, or can then be further functionalised to provide large libraries of molecules with a wide range of potential applications, for example in drug screening.

SUMMARY OF THE INVENTION

In a first aspect, the invention provides a method of synthesis of a bicyclic or polycyclic compound of general formula I or general formula II

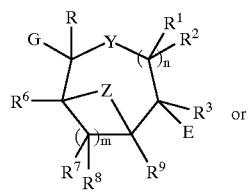

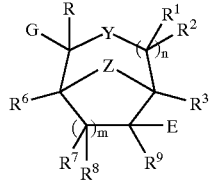

in which:
E represents an electrophile;
each of R, $R^1$, $R^2$, $R^3$, $R^6$, $R^7$, $R^8$ and $R^9$ independently represents hydrogen, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio and acylthio, each of which may optionally be substituted, and wherein any two or more of R, $R^1$–$R^3$ and $R^6$–$R^9$ may form an optionally substituted alkyl, alkenyl or alkynyl chain, which chain may also optionally include one or more O, N or S atoms therein;
Y represents $C(R^{12})R^{13}$, O, $NR^{14}$, or S, wherein $R^{12}$, $R^{13}$ and $R^{14}$ each independently have the same definition as R;
G represents W or X;
W represents an electron withdrawing group;
X has the same definition as R;
Z represents O, $NR^{15}$, S or $CR^{16}W'$, where $R^{15}$ has the same definition as R and W' has the same definition as W; and
each of n and m represents an integer from 0 to 100;
and the method comprises the steps of
(a) activating a compound of general formula III;

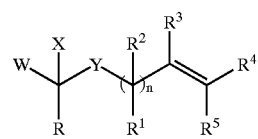

in which R, $R^1$–$R^3$, W, X and Y are as defined above for the compounds of formulae I and II, and $R^4$ and $R^5$ each independently have the same definition as R;

(b) subjecting a compound of general formula IV to nucleophilic addition by the activated form of compound III;

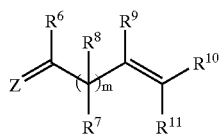

in which $R^6$–$R^{11}$ and Z are as defined above for the compounds of formulae I and II, and $R^{10}$ and $R^{11}$ each independently have the same definition as R;

(c) subjecting the product of step (b) to ring closing metathesis; and (d) subjecting the product of step (c) to stereoselective ring closure.

It will be understood by reference to the definitions for substituents R, $R^1$–$R^3$ and $R^6$–$R^9$ that the compound of formula I or formula II may contain further rings in addition to the two rings formed in the method defined above.

The term "alkyl" used either alone or in a compound word such as "optionally substituted alkyl" or "optionally substituted cycloalkyl" denotes straight chain, branched or mono- or poly-cyclic alkyl. It will be clearly understood that the chain length of the alkyl group is not critical, and that in contrast to other types of organic syntheses, there appears to be no practicable upper limit. However, preferably the alkyl is $C_{1-30}$ alkyl or cycloalkyl. Examples of straight chain and branched alkyl include methyl, ethyl, propyl, isopropyl, butyl, isbutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimetylpentyl, 1,2-dimethylpentyl, 1,3-dimethylpentyl, 1,4-dimethylpentyl, 1,2,3-trimethylbutyl, 1,1,2-trimethylbutyl, nonyl, 1-, 2-, 3-, 4-, 5-, 6- or 7-methyloctyl, 1-, 2-, 3-, 4- or 5-ethylheptyl, 1-2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include cyclopropyl, cyclobutyl, cyclopentyl, cyclohexyl, cycloheptyl, cyclooctyl, cyclononyl and cyclodecyl and the like. The alkyl may optionally be substituted by any non-deleterious substituent.

The term "alkenyl" used either alone or in compound words such as "alkenyloxy" denotes groups formed from straight chain, branched or cyclic alkenes including ethylenically mono-, di- or poly-unsaturated alkyl or cycloalkyl groups as defined above, preferably C2–20 alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexaidenyl, 1,3-cycloheptadienyl, 1,3,5-cycloheptatrienyl and 1,3,5,7-cyclooctatetraenyl.

The term "alkoxy" used either alone or in compound words such as "optionally substituted alkoxy" denotes straight chain or branched alkoxy, preferably C1–30 alkoxy. Examples of alkoxy include methoxy, ethoxy, n-propyloxy, isopropyloxy and the different butoxy isomers.

The term "acyl" used either alone or in compound words such as "optionally substituted acyl" or "optionally substituted acyloxy" denotes carbamoyl, aliphatic acyl group and acyl group containing an aromatic ring, which is referred to as aromatic acyl or a heterocyclic ring which is referred to as heterocyclic acyl, preferably C1–30acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, pentadecanoyl, hexadecanoyl, heptadecanoyl, octadecanoyl, nonadecanoyl and icosangyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutyl, phenylpentanoyl and phenylhexanoyl) and naphthylalkanoyl (e.g. naphthylacetyl, naphthylpropanoyl and naphthylbutanoyl); aralkenoyl such as phenylalkenoyl (e.g. phenylpropenoyl, phenylbutenoyl, phenylmethacrylyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and naphthyloxycarbonyl; aryloxyalkanoyl such as phenoxyacetyl and phenoxypropionyl; arylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and naphthylsulfonyl; heterocycliccarbonyl; heterocyclicalkanoyl such as thienylacetyl, thienylpropanoyl, thienylbutanoyl, thienylpentanoyl, thienyihexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The term "aryl" used either alone or in compound words such as "optionally substituted aryl", "optionally substituted aryloxy" or "optionally substituted heteroaryl" denotes single, polynuclear, conjugated and fused residues of aromatic hydrocarbons or aromatic heterocyclic ring systems. Examples of aryl include phenyl, biphenyl, terphenyl, quaterphenyl, phenoxyphenyl, naphtyl, tetrahydronaphthyl, anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, pyrrolyl, furanyl, imadazolyl, pyrrolydinyl, pyridinyl, piperidinyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Preferably, the aromatic heterocyclic ring system contains 1 to 4 heteratoms independently selected from N, O and S and containing up to 9 carbon atoms in the ring.

The term "heterocyclyl" used either alone or in compound words such as "optionally substituted saturated or unsaturated heterocyclyl" denotes monocyclic or polycyclic heterocyclyl groups containing at least one heteroatom atom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, phosphorus-containing groups and the like. A "non-deleterious subsitituent" refers to any of the substituents outlined above which does not interfere with the formation of the target compound or has not interfered with the formation of the subject compound. Preferred substituents are selected from the group consisting of halo, hydroxy, amino, nitro, cyano, mono- or di alkylamino, mono- or diarylamino, alkoxy, aryloxy, thioalkoxy, thiaryloxy, or is one or more alkyl, alkenyl, alkynyl, aryl, or alkylheteryl groups, each of which may be saturated or unsaturated.

"Halo" or halogen means chloro, bromo, fluoro, or iodo.

The electrophile may be of any suitable known type, such as, for example, those electrophiles disclosed in J. March, "Advanced Organic Chemistry: Reactions, Mechanisms and Structure", 4$^{th}$ Edition, John Wiley & Sons, New York,1992 p 205. The electrophile may be organic or organometallic. Preferably the electrophile is selected from the group consisting of H, hydroxy, alkoxy, acyl, acyloxy, alkylsulphonyloxy, arylsulphenyloxy, hetercyclyloxy, carboalkoxy, carboaryloxy, alkylthio, benzylthio, acylthio, cyano, halo, aryloxy, benzyloxy, haloalkoxy, haloalkenyloxy, haloaryloxy, acids or esters of phosphorous or sulphur, and metal salts, such as AuHal, HgHal, PdHal, SHal, and SeHal.

The electron-withdrawing group or groups (W and W') may also be of any suitable known type, such as, for example, one of the electron-withdrawing groups disclosed in J. March, "Advanced Organic Chemistry: Reactions, Mechanisms and Structure", 4$^{th}$ Edition, John Wiley & Sons, New York, 1992 pp18–19. The electron-withdrawing group could therefore be selected from the group consisting of alkenyl, alkynyl, aryl, halo, haloalkenyl, haloalkynyl, haloaryl, alkoxy, alkenyloxy, aryloxy, benzyloxy, haloalkoxy, haloalkenyloxy, haloaryloxy, nitro, nitroalkenyl, nitroalkynyl, nitroaryl, nitroheterocyclyl, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulfonyloxy, arylsulfenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio and acylthio, alkylsulfinyl, arylsulfinyl, alkylsulfenyl, arylsulfenyl, alkyphosphonyl, arylphosphonyl, each of which may optionally be substituted.

Preferably, the electron withdrawing group contains a chiral auxiliary. A chiral auxiliary is a group which is attached temporarily to a molecule in order to influence the stereoselectivity of one or more synthetic transformations. A full description of the way in which chiral auxiliaries influence stereoselectivity of reactions can be found in G. Lin, Y. Li. A. S. C. Chan, Principals and Applications of Asymmetric Synthesis, Wiley Interscience, New York, 2001, pp49–53, D. A. Evans, V. J. Nelson, E. Vogel, T. R. Taber, J. Am. Chem, Soc., 1981, 103, 3099–3111, W. Oppoizer, J. Blagg, I. Rodriguez, e. Walther, J. Am. Chem,. Soc., 1990, 112, 2767–2772 and D. A. Evans, Aldrichimica Acta., Vol.15. No. 2, 1982, p319. Once the reaction or synthetic transformation has been completed, the auxiliary can be removed, and sometimes recycled, under very mild conditions which do not affect the rest of the molecule in any way. Suitable chiral auxiliaries may be selected from one of the chiral auxiliaries disclosed in the Lin et al text referred to above. Some specific examples used by the applicant are Oppolzer's sultam (Oppolzer et al., 1990),

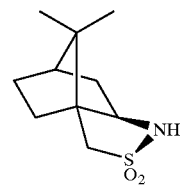

Evans' auxiliary (Evans et al., 1982),

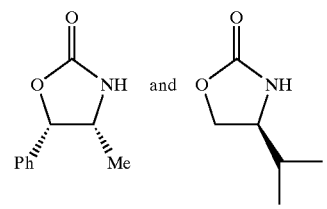

and Nagao's auxiliary (Nagao et al., 1992)

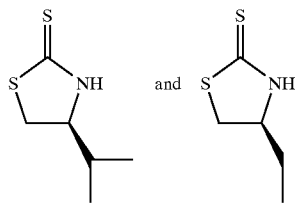

In each of these three examples, the auxiliary is attached to the compound via the nitrogen atom (with removal of the hydrogen atom).

A chiral auxiliary may also be advantageously used in other locations of the compound during synthesis.

Preferably each of n and m represents an integer from 0 to 50, more preferably 0 to 25.

The compound may be a carbocycle, oxacycle, azacycle or thiacycle, and is preferably a compound selected from the group consisting of monosaccharides, oligosaccharides, tropane alkaloids, cyclic α- and/or β-amino acids, squalestatins, zaragozic acids, fumagillins, and analogues thereof.

Regarding steps (a) and (b), the methods employed for activating the compound of general formula III and conducting the nucleophilic addition may be varied as necessary according to the nature of the electron withdrawing group W. Suitable methods are well known in the art, for example by reference to March, J. in *Advanced Organic Chemistry*, Third Ed., John Wiley & Sons Inc., 1985, Chapter 10: Aliphatic Nucleophilic Substitution p 255–447, and Chapter 16: Addition to Carbon Hetero Multiple Bonds p 780–873.

One option for conducting steps (a) and (b) requires X to be hydrogen, and the method involves treating the compound of formula III with a base in order to generate the corresponding enolate. In this embodiment, G in the compound of formula I or II will be the electron withdrawing group W.

Another option for conducting steps (a) and (b) the reaction requires W to be a halogen, and the method involves employing metal-halogen exchange to generate the corresponding organometallic reagent or Grignard reagent. In this situation, the electron withdrawing group is converted to the Grignard reagent, and W is therefore detached from the compound. Accordingly, if this synthetic route is utilised, in this embodiment, G in the compound of formula I or II will be X.

Regarding step (c), the term "ring closing metathesis" is to be understood to mean the coupling of two tethered alkenes to form a ring comprising a new alkene, with concomitant loss of an alkene (Grubbs and Chang 1998; Schuster and Bleichert 1997; Schwab et al, 1996).

Enantiomeric selectivity in step (b) may be achieved in two ways. Either one or both of the starting compounds of formulae III and IV is chiral, or an enantiomerically-enriched additive system is used to promote stereoselective coupling of the compounds of formulae III and IV.

The additive may be a catalyst or a promoter, and may be present in an amount ranging from sub-stoichiometric to stoichiometric or greater. Thus the additive may be a catalyst. The additive includes but is not limited to Sn (II) salts in combination with chiral, non-racemic diamine ligands (Kobayashi at al, 1989, 1994), chiral, non-racemic Binol metal complexes (Yamada et al, 1998; Mikami et al, 1993) and chiral, non-racemic metal complexes of semicorrins (Evans, 1999).

The final step of the procedure involves the formation of the second ring by creating a bridge across the cycloalkene, with the consequent saturation of the alkenyl double bond. The cyclisation reactions are diastereoselective, ie they rely on the structures of the starting materials to induce chirality in the newly-formed ring. A typical example of this reaction is intramolecular oxymercuration. Suitable reagents for conducting this final step include electrophiles, such as metal salts, eg $HgCl_2$, $Hg(OCOR)_2$, $PdCl_2$; halogens, eg $Br_2$, $Cl_2$, $I_2$; peracids, eg $RCO_3H$, $ArCO_3$; and electrophilic selenating reagents eg PhSeBr.

The bond formed between the carbon atoms carrying substituents W and Z generates new stereochemistry. If W in compound III is an acid and R is $NH_2$, the product will be an α-amino acid. If Z contains N, then the product is a β-amino acid. If R and Z both contain N, then the product is an α, β-diamino acid.

The general synthetic strategy is outlined in Scheme 1:

Scheme 1

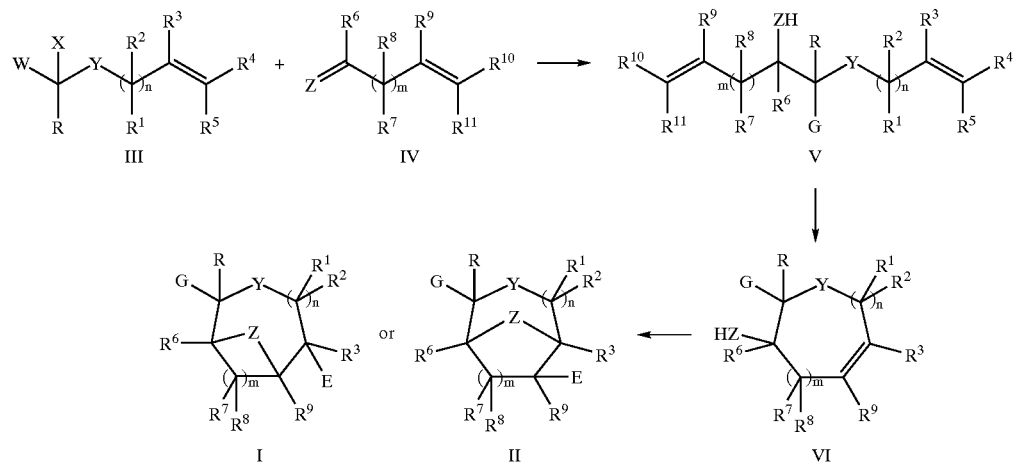

in which:

E, R, $R^1$–$R^{11}$, G, W, X, Y and Z are as defined above.

It has also been appreciated by the present applicant that a similar method could be used to form compounds closely corresponding to those of formula I and/or formula II in which Z is replaced by Z'. This method involves the same reactions steps as the method set out above, with the exception that the compound of formula IV containing a double bond to Z is replaced by a compound of formula VII containing a triple bond to Z'. Accordingly, in this embodiment, Z' is selected from the group consisting of CW" and N, in which W" has the same definition as W in the compounds of formulae I and II.

This reaction is set out in Scheme 2:

carbon atom $C^a$ being to the same side of the alkenyl double bond as carbon atom $C^b$;
(c) activating carbon atom $C^d$ in said first compound;
(d) subjecting the second compound to nucleophilic addition by the activated form of the first compound to connect carbon atoms $C^d$ and $C^a$
(e) subjecting the product of step (d) to ring closing methathesis to thereby connect carbon atoms $C^b$ and $C^c$ via a double bond; and
(f) subjecting the product of step (e) to stereoselective ring closure to form a bridge between $C^a$ and one or both of $C^b$ and $C^c$ with the loss of the alkenyl bond between $C^b$ and $C^c$ to yield said compound containing two rings.

It will be understood that the two rings formed in this reaction may be in addition to other rings already present in Scheme 2:

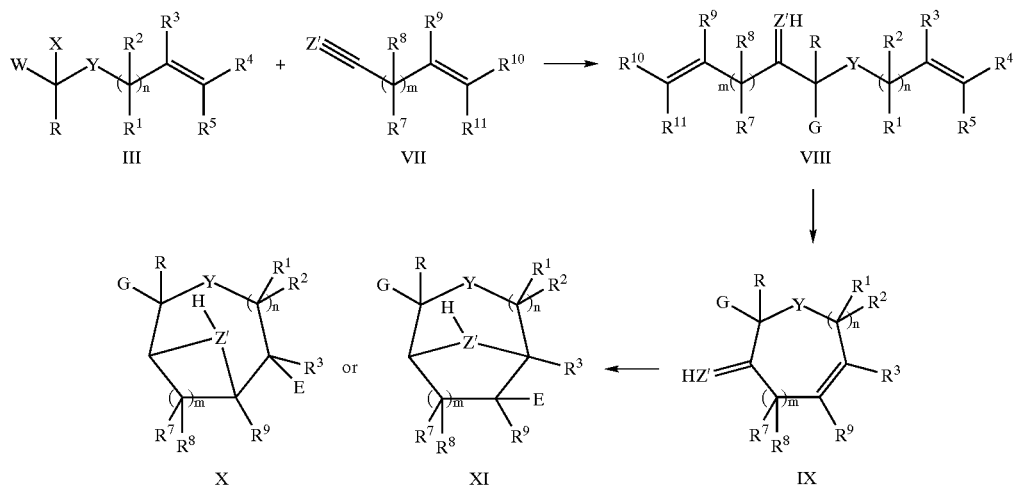

in which:

E, R, $R^1$–$R^{11}$, G, X, W and Y are as defined above for the compounds of formulae I, II, III and IV, and Z' is N or CW", where W" has the same definition as W.

It will be understood that the compounds of formulae I, II, X and XI may be subjected to further reactions to form derivatives thereof. For instance, the electrophile E may be replaced by a substituent $R^{19}$ having the same definition as R in formulae I and II.

It will be appreciated by persons skilled in the art of the invention that the synthetic procedure developed by the applicant for the formation of two rings in a compound with high stereoselectivity can be applied to synthesis of a very large range of compounds without being restricted to the structures outlined above.

According to a third aspect, the present invention accordingly provides a method of forming a compound with two rings, with carbon atoms $C^a$ and $C^b$, or carbon atoms $C^a$ and $C^c$, being common to the two rings, the method comprising:

(a) providing a first compound containing carbon atom $C^c$ as an alkenyl carbon atom at one position in the first compound, and a carbon atom $C^d$ at another position in the compound with an electron withdrawing group attached thereto, the carbon atom $C^d$ being to the same side of the alkenyl double bond as the carbon atom $C^c$;
(b) providing a second compound containing a carbon atom $C^b$ as an alkenyl carbon atom at one position in the second compound, and a carbon atom $C^a$ at another position in the compound with a double bond or a triple bond between carbon atom $C^a$ and a substituent on $C^a$, the the first and second compounds which form the starting materials for the reaction.

The fragments of the first compound between carbon atoms $C^c$ and $C^d$ may be of any constitution that does not interfere with the subsequent reactions being conducted to form the target compound. Accordingly, the fragment may contain a substituted or unsubstituted, branched, unbranched or cyclic hydrocarbon group, optionally interspersed with one or more O, N and S atoms. The substituents may be any one of the non-deleterious substituents as defined above, or may be the protected form of one of the broader range of possible substitutents that could interfere in the reactions for forming the two rings if not protected.

The fragments of the second compound between carbon atoms $C^a$ and $C^b$ may likewise be of any constitution that does not interfere with the subsequent reactions being conducted to form the target compound. Accordingly, the fragment may contain a substituted or unsubstituted, branched, unbranched or cyclic hydrocarbon group, optionally interspersed with one or more O, N and S atoms. The substituents may be any one of the non-deleterious substituents as defined above, or may be the protected form of one of the broader range of possible substitutents that could interfere in the reactions for forming the two rings if not protected.

In step (d), the end fragments joined to $C^b$ and $C^c$ via the respective double bonds prior to the ring closing metathesis are disconnected. Accordingly these fragments of the first and second compounds may be of any constitution provided that they do not interfere with steps (c), (d) and (e).

The electron withdrawing group attached to $C^d$ in the first compound can be any of the well-known electron withdrawing groups known in the art, and therefore has the same definition as W in formulae I and II outlined above. Steps (c) and (d) may be conducted by activating the first compound using a base to form an enolate and reacting this with the second compound. In one preferred embodiment of this technique for conducting these steps, the electron withdrawing group includes a chiral auxiliary radical. Chiral auxiliaries are described in detail above. In an alternative method for conducting steps (c) and (d), the electron-withdrawing group is a halogen, and $C^d$ is activated by reacting the first compound with magnesium to form the corresponding organomagnesium halide, or by reacting the first compound with another suitable reagent (such as lithium metal) to form the corresponding organometallic reagent.

The substituent attached to carbon atom Ca of the second compound is preferably selected from the group consisting of O, $NR^{17}$, $CR^{18}W^x$ and S, when the substituent is connected via a double bond, and N or $CW^y$ when the substituent is connected via a triple bond, wherein $R^{17}$ and $R^{18}$ each have the same definition as R in formula I, and $W^x$ and $W^y$ each have the same definition as W in formula I.

The preferred features of the method of the third aspect of the invention will be readily apparent from the description of the first aspect of the invention outlined above.

Selected examples of target compounds and their starting materials are set out in Table 1 below. The target compounds may be derivatives of the compounds of formulae I or II. In each case the substituents R, W, X, G and Z as well as the descriptors m and n have the same definitions as those set out above for the compounds of formulae I and II. Only skeleton structures for the target molecules are shown; it will be clearly understood that each may contain one or more of the substituents $R^1$ to $R^{11}$ and E set out above for formulae I and II. It is also to be noted that some of the compounds set out below may include further hydrocarbon rings, as denoted by the hydrocarbon groups with the descriptor p. "p" has the same definition as m and n in Formulae I and II.

TABLE 1

Examples of target molecules

| Compound III | Compound IV | Targets |
|---|---|---|

TABLE 1-continued

Examples of target molecules

| Compound III | Compound IV | Targets |
|---|---|---|

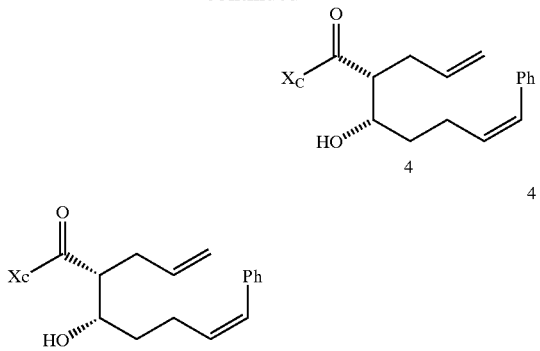

The compounds described herein are useful either as lead candidates for pharmaceutical or agrochemical development, or as intermediates in synthesis of other compounds. Methods of screening of candidate compounds for useful biological or pharmacological activity are very widely known in the art. See for example Tait (1992). The assays to be used and the threshold activity regarded as useful will depend on the nature of the compound and the specific assay and activity used.

Thus in a second aspect, the invention provides a library of compounds suitable to be tested for a desired biological or pharmacological activity, comprising a plurality of compounds prepared by the method of the invention.

Some of the compounds of general formula I or general formula II are novel, and it will be clearly understood that these are within the scope of the invention. In particular the compounds listed in Table I are within the scope of the invention.

Preferably the compound is in enantiomerically pure form. More preferably the compound is produced by the method of the invention.

For the purposes of this specification it will be clearly understood that the word "comprising" means "including but not limited to", and that the word "comprises" has a corresponding meaning.

DETAILED DESCRIPTION OF THE INVENTION

The invention will now be described in detail by way of reference only to the following non-limiting examples.

EXAMPLE 1

Synthesis of Aldol Adduct (4)

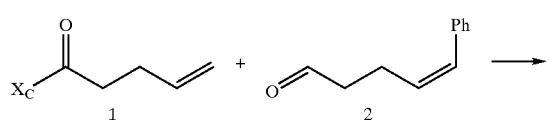

-continued

A solution of diethyl boron triflate was generated by dropwise addition of freshly distilled triflic acid (440 μl, 5.0 mmol) to triethyl borane (1M in hexane, 5 ml, 5.0 mmol). The solution was stirred at RT for 20 minutes until mostly homogeneous. If the solution is not homogeneous, it may be warmed at approx. 40° for 20 min.

The triflate solution was cooled to −5° and a solution of the acyl sultam (1) (743 mg, 2.5 mmol) in dichloromethane (5 ml), followed by a solution of NN-di isopropyl ethylamine (1M in dichloromethane, 5 ml, 5.0 mmol) were added. After stirring at −5° for 20 minutes the solution was cooled to −78° and a solution of the aldehyde (2) (610 mg, 3.8 mmol) in dichloromethane (1 ml) was added. After stirring for 2 hours the reaction was quenched by addition of 0.5M pH 7 phosphate buffer (10 ml) and left to warm to RT.

The mixture was taken up in ether (30 ml), the aqueous layer separated and the organic layer washed with sat. $NH_4Cl$ (2×50 ml). After drying ($MgSO_4$) and removal of solvent in vacuo (at ambient temperature) the aldol adduct was purified by column chromatography eluting hexane/ethyl acetate (4:1). $R_f$ (0.25) in hexane/ethyl acetate (5:1). The aldol adduct (4) was obtained as a colourless crystals 843 mg, 77%. mp 85–87.

$[a_D]$−58° (c 1.0, $CH_2Cl_2$).

IR (nujol/$CH_2Cl_2$ film): 3495, 2923, 2854, 1685, 1461, 1377, 1335, 1267, 1237, 1213, 1166, 1134, 1066, 992, 917, 769, 740, 701 $cm^{−1}$.

$^1$H NMR (300 MHz, $CDCl_3$) d 0.97 (s, 3H, CH3), 1.15 (s, 3H, CH3), 1.36 (m, 2H, $CH_2$), 1.58 (m, 1H, HCH), 1.76 (m,

1H, HCH), 1.90 (m, 3H, CH₂ and CH), 2.02 (d, 2H, J=6.7 Hz, CH₂), 2.50 (m, 4H, 2×CH₂), 3.24 (m, 1H, CHCO), 3.44 and 3.52 (AB quartet, 2H, J=13.7 Hz, CH₂SO₂), 3.90 (t, 1H, J=6.6 Hz, CHN), 4.00 (dt, 1H, J=3.6, 9.3 Hz, CHOH), 4.98 (d, 1H, J=10.2 Hz, H2), 5.08 (dd, 1H, J=1.0, 17.0 Hz, H1), 5.66 (dt, 1H, J=7.4, 11.7 Hz, H5), 5.84 (m, 1H, H3), 6.43 (d, 1H, J=11.5 Hz, H4), 7.30 (m, 5H, Ph).

$^{13}$C NMR (50 MHz, CDCl₃) d 19.8 (8), 20.8 (9), 25.2 (5), 26.3 (CH₂), 32.1 (CH₂), 32.9 (CH₂), 34.3 (6), 38.2 (3), 44.6 (4), 47.6 (7), 48.1 (1), 49.2 (CHCO), 53.2 (10), 65.2 (2), 70.4 (CHOH), 117.4 (CH₂=C), 126.4 (Ph), 128.0 (Ph), 128.7 (Ph), 129.3 (CH=C), 131.9 (CH=C), 135.0 (CH=C), 137.5 (Ph), 175.1 (CO).

MS (Electro spray) 458.4 (M+1, 100%).

Anal. calcd. for C₂₆H₃₅NSO₄: C, 68.24; H, 7.71; N, 3.06: Found: C, 68.04; H, 7.60; N, 3.13.

EXAMPLE 2

Synthesis of Aldol Adduct (5)

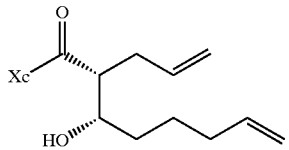

In a similar fashion to (4) a solution of diethyl boron triflate was generated from triflic acid (550 ml, 6.2 mmol) and triethyl borane (1M in hexane, 6.2 ml, 6.2 mmol). To this solution was added the acyl sultam (1) (993 mg, 3.1 mmol) in dichloromethane (10 ml), followed by a solution of NN-diisopropylethylamine (1.1 ml, 6.2 mmol) in dichloromethane (1 ml), and the aldehyde (3) (616 mg, 6.28 mmol). The reaction was quenched by addition of 0.5M pH 7 phosphate buffer (12 ml), taken up in ether (30 ml), the aqueous layer separated and the organic layer washed with sat. NH₄Cl (2×50 ml). After drying (MgSO₄) and removal of solvent in vacuo (at ambient temperature) the aldol adduct was purified by column chromatography eluting hexane/ethyl acetate (5:1).

The aldol adduct (5) was obtained as an oil 853 mg, 70%.

R$_f$ (0.58) in hexane/ethyl acetate (2:1).

[a$_D$]-78° (c 1.4, CH₂Cl₂).

IR (nujol/CH₂Cl₂ film): 3528, 3075, 2926, 1682, 1458, 1415, 1377, 1336, 1266, 1236, 1213, 1166, 1135, 1065, 1040, 992, 912, 739 cm$^{-1}$.

$^1$H NMR (300 MHz, CDCl₃) d 0.96 (s, 3H, CH₃), 1.15 (s, 3H, CH₃), 1.30–1.68 (m, 7H, 3×CH₂ and CH), 1.82–2.34 (m, 7H, 3×CH₂ and OH), 2.50 (m, 2H, CH₂), 3.23 (m, 1H, CHCO), 3.42 and 3.46 (AB quartet, 2H, J=12.5 Hz, CH₂SO₂), 3.90 (t, 1H, J=5.0 Hz, CHN), 3.96 (m, 1H, CHOH), 4.91–5.13 (m, 4H, 2×C=CH₂), 5.82 (m, 2H, 2×CH=C)

$^{13}$C NMR (50 MHz, CDCl₃) d 20.6 (8), 21.5 (9), 25.9 (CH₂) 27.0 (5), 32.4 (6), 33.6 (CH₂), 34.1 (CH₂), 34.2 (CH₂), 38.9 (3), 45.3 (4), 48.3 (7), 48.8 (1), 49.4 (CHCO), 53.8 (10), 65.9 (2), 72.1 (CHOH), 115.1 (CH₂=C), 117.9 ( CH₂=C), 135.6 (CH=C), 139.1 (C175.9 (CO).

EXAMPLE 3

Synthesis of Cycloheptene Compound (6)

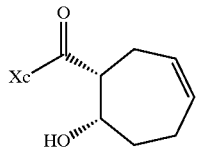

The aldol adduct (4) (98 mg, 0.2 mmol) was dissolved in degassed dichloromethane (15 ml) under argon. A solution of Grubbs' catalyst (17 mg, 0.02 mmol) in dichloromethane (1 ml) was added and the reaction stirred overnight. Evaporation of the solvent, followed by chromatography eluting hexane/ethyl acetate (4:1), gave the cycloheptene (6) as colourless crystals 59 mg, 79%.

R$_f$ (0.17) in hexane/ethyl acetate (4:1), mp 141–143°.

[a$_D$]-40° (c 0.4, CH₂Cl₂).

IR (nujol/CH₂Cl₂ film): 3512, 2924, 2854, 1653, 1456, 1411, 1377, 1327,1289, 1268, 1237, 1219, 1165, 1139, 1122, 1072, 1002, 945, 772, 737, 706 cm$^{-1}$.

$^1$H NMR (300 MHz, CDCl₃) d 0.98 (s, 3H, CH₃), 1.16 (s, 3H, CH₃), 1.36 (m, 2H, CH₂), 1.58 (m, 1H, CH), 1.85–2.05 (m, 8H, 4×CH₂), 2.58 (m, 1H, HCH), 2.92 (m, 1H, HCH) 3.08 (dt 1H, J=1.3, 11.2 Hz, CHCO), 3.44 and 3.52 (AB quartet, 2H, J=13.8 Hz, CH₂SO₂), 3.84 (t, 1H, J=1.6 Hz, CHOH), 3.88 (t, 1H, J=6.4 Hz, CHN), 4.38 (s, 1H, OH), 5.85 (m, 2H, CH=CH).

$^{13}$C NMR (75 MHz, CDCl₃) d 20.0 (8), 20.9 (9), 21.0 (CH₂), 24.9 (CH₂), 26.5 (5), 31.9 (CH₂), 32.9 (6), 38.4 (3), 44.6 (4), 47.8 (7), 47.9 (CHCO), 48.4 (1), 53.1 (10), 64.9 (2), 68.9 (CHOH), 129.3 (CH=C), 134.0 (CH=C), 176.1 (CO).

Exact mass calcd. for C₁₈H₂₇NSO₄Na (M+Na⁺) 376.4737, found 376.1539.

EXAMPLE 4

Synthesis of Cyclooctene Compound (7)

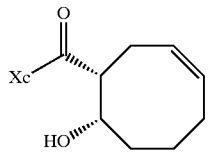

The aldol adduct (5) (484 mg, 1.22 mmol) was dissolved in degassed dichloromethane (390 ml) under argon. A solution of Grubbs' catalyst (85 mg, 0.1 mmol) in dichloromethane (10 ml) was added and the reaction stirred at 50° for 60 hours. Evaporation of the solvent, followed by chromatography eluting hexane/ethyl acetate (4:1), gave the cyclooctene (7) as colourless crystals 193 mg, 43%. R$_f$ (0.55) in hexane/ethyl acetate (2:1), mp 153–155°.

[a$_D$]-78° (c 0.8, CH₂Cl₂).

IR (nujol/CH₂Cl₂ film): 3528, 3055, 2927, 1670, 1456, 1414, 1334, 1285, 1236, 1214, 1165, 1133, 1063, 896, 744 cm$^{-1}$.

$^1$H NMR (300 MHz, CDCl₃) d 0.98 (s, 3H, CH₃), 1.15 (s, 3H, CH₃), 1.32–2.20 (four broad multiplets, 13H, 6×CH₂ and CH), 2.36 (m, 2H, HCH and OH), 2.82 (m, 1H, HCH) 3.27 (dt 1H, J=2.7, 12.2 Hz, CHCO), 3.42 and 3.54 (AB quartet, 2H, J=13.5 Hz, CH$_2$SO$_2$), 3.85 (t, 1H, J=5.4 Hz, CHN), 4.18 (dd 1H, J=2.7, 8.1 Hz, CHOH), 5.72 (m, 2H, CH=CH).

$^{13}$C NMR (75 MHz, CDCl$_3$) d 19.9 (8), 21.0 (9), 25.7 (CH$_2$), 25.9 (CH$_2$), 26.2 (CH$_2$), 26.5 (5), 31.4 (CH$_2$), 32.0 (6), 38.5 (3), 44.7 (4), 47.8 (7), 48.3 (1), 50.8 (CHCO), 53.2 (10), 65.2 (2), 70.9 (CHOH), 127.3 (CH=C), 131.8 (CH=C), 175.1 (CO).

Exact mass calcd. for C$_{19}$H$_{29}$NSO$_4$ (M$^+$) 367.519, found 368.188.

EXAMPLE 5

Synthesis of Bicyclic Mercurial Compound (8)

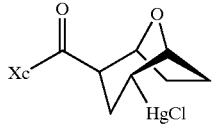

The cycloalkene (6) (109 mg, 0.31 mmol) was dissolved in dichloromethane (25 ml) and Hg(OAc)$_2$ (99 mg, 0.31 mmol) was added. The mixture was stirred at RT overnight after which a solution of sat. NaCl (10 ml) was added and the reaction stirred for at least 1 hour more.

After separation of the organic phase, re-extraction with dichloromethane (5 ml), drying (MgSO$_4$) and evaporation of solvent in vacuo, a mixture of bicyclic mercurials (8) and (9) was obtained in quantitative yield. $^1$H NMR of this mixture showed the ratio of (8) to (9) as 4:1. Recrystallisation of this mixture (dichloromethane/hexane) gave (8) as colourless crystals (91 mq, 50%), R$_f$ (0.28) in hexane/ethyl acetate (1:1). Slow crystallisation of a dichloromethane solution of (8) in the presence of ethyl acetate vapour gave crystals suitable for x-ray. mp 154–156°.

[a$_D$]+19.4° (c 1.0, CH$_2$Cl$_2$).

IR (nujol): 3500, 2924, 2854, 1695, 1461, 1378, 1318, 1203, 1127 cm$^{-1}$.

$^1$H NMR (300 MHz, CDCl$_3$) d 0.97 (s, 3H, CH$_3$), 1.14 (s, 3H, CH$_3$), 1.38 (m, 2H, CH$_2$), 1.90 (m 5H, 2×CH$_2$ and CH), 2.15 (m 5H, 2×CH$_2$ and HCH), 2.53 (dt, 1H, J=6.7, 13.7 Hz, HCH), 2.96 (d 1H, J=6.5 Hz CHHg), 3.44 and 3.49 (AB quartet, 2H, J=13.9 Hz, CH$_2$SO$_2$), 3.53 (m, 1H, CHCO), 3.93 (t, 1H, J=6.3 Hz, CHN), 4.58 (m, 1H, CHO), 4.65 (m, 1H, CHO).

$^{13}$C NMR (75 MHz, CDCl$_3$) d 19.9 (8), 21.1 (9), 26.5 (5), 29.6 (CH$_2$), 29.7 (CH$_2$) 29.9 (CH$_2$), 32.9 (6), 38.8 (3), 44.6 (4), 47.4 (CHCO), 47.8 (7), 48.4 (1), 53.1 (10), 55.0 (CHHg), 65.6 (2), 74.9 (CHO), 78.3(CHO), 171.6(CO).

Anal. Calcd. for C$_{18}$H$_{26}$NSO$_4$HgCl: C, 36.74; H, 4.45; N, 2.38: Found: C, 36.75, H, 4.57; N, 2.57.

Bicyclic Mercurials (10) and (11)

The cycloalkene (7) (160 mg, 0.43 mmol) was dissolved in dichloromethane (40 ml) and Hg(OAc)$_2$ (153 mg, 0.48 mmol) was added. The mixture was stirred at RT overnight after which a solution of sat. NaCl (10 ml) was added and the reaction stirred for at least 1 hour more.

After separation of the organic phase, re-extraction with dichloromethane (10 ml), drying (MgSO$_4$) and evaporation of solvent in vacuo, a mixture of bicyclic mercurials (10) and (11) was obtained (205 mg, 97%.) $^1$H NMR of this mixture showed the ratio of (10) to (11) as 2:1. Chromatography, eluting hexane/ethyl acetate (2:1), gave bicyclic mercurial (10) (105 mg, 40%), R$_f$ (0.21) in hexane/ethyl acetate (2:1) and bicyclic mercurial (11) (60 mg, 23%), R$_f$ (0.27) in hexane/ethyl acetate (2:1).

EXAMPLE 6

Synthesis of Bicyclic Mercurial Compound (10)

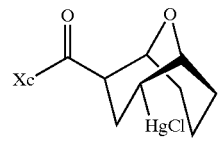

Amorphous solid following trituration with Et$_2$O. mp 135–145° dec.

[a$_D$]–2° (c 1.0, CH$_2$Cl$_2$)

IR (nujol/CH$_2$Cl$_2$ film): 3438, 2926, 2854, 1686, 1458, 1377, 1327, 1265, 1235, 1211, 1164, 1132, 1060, 1023, 982, 845, 772, 736 cm$^{-1}$.

$^1$H NMR (300 MHz, CDCl$_3$) d 0.97 (s, 3H, CH$_3$), 1.14 (s, 3H, CH$_3$), 1.40 (m, 2H, CH$_2$), 1.72 (m, 2H, CH$_2$), 1.88 (m, 3H, CH$_2$ and CH), 2.02–2.36 (m, 7H, 3×CH$_2$ and HCH), 2.86 (dq 1H, J=6.7, 12.2 Hz, HCH) 3.12 (m, 1H, CHHg), 3.45 and 3.51 (AB quartet, 2H, J=13.8 Hz, CH$_2$SO$_2$), 3.62 (pent., 1H, J=6.0 Hz, CHCO), 3.91 (t, 1H, J=6.4 Hz, CHN), 4.22 (bt 1H, J=5.8 Hz, CHO), 4.28 (m, 1H, CHO).

$^{13}$C NMR (75 MHz, CDCl$_3$) d 18.2 (CH$_2$), 19.9 (8), 21.1 (9), 26.4 (5), 29.2 (CH$_2$), 29.6 (CH$_2$), 32.8 (6 and CH$_2$), 38.7 (3), 44.6 (4), 45.1 (CHCO), 47.8 (7), 48.4 (1), 52.9(CHHq), 53.1 (10), 65.3 (2), 66.7 (CHO), 69.4 (CHO), 172.7 (CO).

Anal. Calcd. for C$_{19}$H$_{28}$NSO$_4$HgCl: C, 37.87; H, 4.68; N, 2.33: Found: C, 38.13, H, 4.84; N, 2.33.

EXAMPLE 7

Synthesis of Bicyclic Mercurial Compound (11)

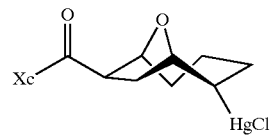

Colourless crystals from CH$_2$Cl$_2$/EtOH. mp 129–131° dec.

[a$_D$]–54° (c 1.0, CH$_2$Cl$_2$).

IR (nujol/CH$_2$Cl$_2$ film): 3441, 2925, 2634, 1686, 1459, 1377, 1330, 1264, 1213, 1165, 1132, 1053, 986, 904, 743 cm$^{-1}$.

$^1$H NMR (300 MHz, CDCl$_3$) d 0.98 (s, 3H, CH3), 1.15 (s, 3H, CH$_3$), 1.40 (m, 2H, CH$_2$), 1.50–2.90 (five multuplets, 13H, 6×CH$_2$ and CH), 2.90 (dt 1H, J=4.3, 11.6 Hz CHHg), 3.42 and 3.56 (AB quartet, 2H, J=13.7 Hz, CH$_2$SO$_2$), 3.60 (m, 1H, CHCO), 3.88 (t, 1H, J=6.3 Hz, CHN), 4.80 (d, 1H, J=8.4 Hz, CHO), 4.86 (pent., 1H, J=4.3 Hz, CHO).

$^{13}$C NMR (75 MHz, CDCl$_3$) d 20.0 (8), 21.0 (9), 26.5 (5), 26.6 (CH$_2$), 30.1 (CH$_2$), 32.9 (6), 34.4 (CH$_2$), 37.5 (CH$_2$), 38.4 (3), 44.6 (4), 47.8 (7), 48.5 (1), 53.2 (10), 54.1 (CHCO), 60.2(CHHg), 65.5(2), 79.3(CHO), 81.9(CHO), 172.7(CO).

Anal. Calcd. for C$_{19}$H$_{28}$NSO$_4$HgCl: C, 37.87; H, 4.68; N, 2.33: Found: C, 37.89, H, 4.77; N, 2.39.

EXAMPLE 8

Synthesis of Bicyclic Compound (12)

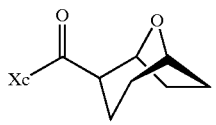

A solution of the bicyclic mercurial (8) (178 mg, 0.3 mmol), AIBN (59 mg, 0.36 mmol), in toluene (6 ml) was stirred under argon and tributyl tin hydride (1 ml, 3.6 mmol) was added. The solution was then stirred at RT overnight, warmed between 70–900 for 1 hour, left to cool to RT, $CCl_4$ (1 ml) was added and the reaction stirred for 1 hour more.

After the reaction solution was separated from the mercury residues, it was taken up in dichloromethane (20 ml), washed with 1M KF soln. (20 ml) and water (20 ml). Filtration was necessary to remove unwanted salts and to break up emulsions. After drying ($MgSO_4$) and chromatography eluting hexane/ethyl acetate (2:1), the bicyclic mercurial (8) was obtained as an oil that crystallised on standing 49 mg, 47%. mp 136–138°.

$R_f$ (0.33) in hexane/ethyl acetate (2:1).

$[a_D]$–66.2° (c 1.0, MeOH).

IR ($CH_2Cl_2$ film): 3054, 2962, 1698, 1422, 1329, 1266, 1209, 1132, 1064, 989 cm$^{-1}$.

$^1$H NMR (300 MHz, $CDCl_3$) d 0.96 (s, 3H, $CH_3$), 1.14 (s, 3H, $CH_3$), 1.30 (m, 2H, $CH_2$), 1.50–2.21 (m, 13H, 6×$CH_2$ and CH), 2.87 (dd 1H, J=1.2, 5.7 Hz CHCO), 3.44 and 3.48 (AB quartet, 2H, J=13.8 Hz, $CH_2SO_2$), 3.94 (t, 1H, J=6.6 Hz, CHN), 4.44 (m, 1H, CHO), 4.71 (d, 1H, J=6.9 Hz, CHO).

$^{13}$C NMR (75 MHz, $CDCl_3$) d 19.3 ($CH_2$), 19.9 (8), 20.8 (9), 26.4 (5), 27.5 ($CH_2$), 28.7 ($CH_2$) 29.2 ($CH_2$), 32.8 (6), 38.7 (3), 44.2 (CHCO), 44.5 (4), 47.7 (7), 48.2 (1), 53.1 (10), 65.5 (2), 73.8 (CHO), 74.6 (CHO), 172.7 (CO).

Exact mass calcd. for $C_{18}H_{27}NSO_4$ (M+Na$^+$) 376.4749, found 376.1565.

EXAMPLE 9

Synthesis of Bicyclic Acid Compound (13)

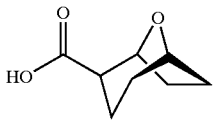

To a chilled solution of the bicyclic (12) (49 mg, 0.14 mmol) in THF (2 ml) and $H_2O$ (0.5 ml), was added successively LiOH (12 mg, 0.28 mmol) and 30% $H_2O_2$ soln. (57 ml, 0.5 mmol). The reaction was left slowly warming to RT and stirring for 2 hours. After acidification with 2M HCl, $H_2O$ (7 ml) was added and the solution was extracted with ethyl acetate (2×7 ml) and dried ($MgSO_4$).

Some of the sultam was removed from the crude mixture by chromatography, eluting hexane/ethyl acetate (1:2); however the acid (13) was finally purified when taken up in 0.5M $NaHCO_3$ (5 ml). This aqueous solution was extracted with dichloromethane (5 ml), acidified by dropwise addition of conc. HCl and extracted with dichloromethane (5×5 ml). The final organic extracts, after drying ($MgSO_4$) and solvent removal, gave the acid (13) 12 mg 55% as an oil that crystallised on standing. Recrystallisation (hexane/ethyl acetate) gave mp 112–114°.

$R_f$ (0.35) in hexane/ethyl acetate (1:3).

$[a_D]$+32.7° (c 0.7, $CH_2Cl_2$).

IR (nujol/$CH_2Cl_2$ film): 3228, 2925, 2854, 1735, 1466, 1377, 1209, 1169, 1106, 1020, 986, 866, 748 cm$^{-1}$.

$^1$H NMR (300 MHz, $CDCl_3$) d 1.32 (m, 1H, HCH), 1.79 (m, 3H, HCH and $CH_2$), 2.02 (m, 4H, 2×$CH_2$), 2.39 (d, 1H, J=5.7 Hz, CHCO), 4.43 (bs, 1H, CHO), 4.77 (d, 1H, J=6.8 Hz, CHO).

$^{13}$C NMR (75 MHz, $CDCl_3$) d 17.2 ($CH_2$), 27.9 ($CH_2$), 28.6 ($CH_2$), 28.7 ($CH_2$), 45.1 (CHCO), 75.6 (CHO), 75.7 (CHO), 177.6 (CO).

Exact mass calcd. for $C_8H_{12}O_3$ (M$^+$), found.

EXAMPLES 10–14

The following reaction scheme was followed to form the bicyclic compound 16:

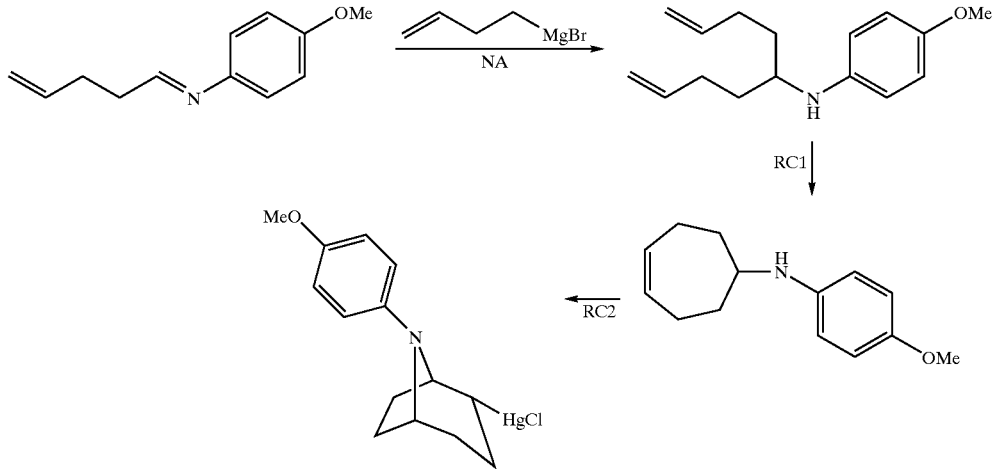

EXAMPLE 10

Synthesis of Diene (14)

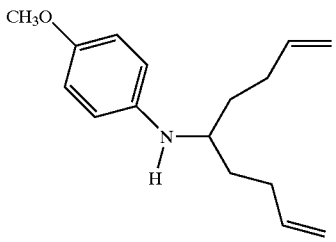

The p-anisidine imine of 4-pentenal was prepared by addition of p-anisidine (458 mg, 3.72 mmol) to an ice cold solution of 4-pentenal (317 mg, 3.72 mmol) in diethylther (3.5 ml). After stirring in the cold for 15 minutes, 4 pellets of KOH were added and the mixture was stirred for an additional 15 minutes. The crude imine solution was obtained by filtering the solution from the solid KOH.

4-Bromo-1-butene (755 µL, 7.4 mmol) was added to a solution of magnesium (200 mg, 8.2 mmol) in dry THF (13 ml) under nitrogen atmosphere with stirring at room temperature. After the magnesium was consumed, the solution was cooled to −30° C. and CuI (1.41 g, 7.4 mmol) was added and stirring was continued for 10 minutes at −30° C. The mixture was cooled to −78° C. and $BF_3OEt$ (910 µL, 9.9 mmol) was slowly added and the mixture was stirred constantly. The crude imine solution (describe above) was added to this mixture and stirred for 10 minutes at −78° C. The mixture was allowed to warm to room temperature slowly with stirring. 10% Aqueous sodium hydroxide (20 mL) was added and the mixture was extracted by ethyl acetate (3×50 mL) and dried over anhydrous magnesium sulfate, concentrated and purified by flash column chromatography (20:1, hexane:ethyl acetate). The diene (14) was obtained as a yellow oil (412 mg, 45%)

$^1$H NMR (200 MHz, $CDCl_3$) δ 1.60 (m, 4H, 2×$CH_2$), 2.01 (m, 4H, 2×$CH_2$), 3.30 (pent, 1H, J=6 Hz, CH), 3.63 (s, 3H, $CH_3$), 5.00 (m, 4H, 2×CH=C), 5.80 (m, 2H, 2×C=CH), 6.53 (d, 2H, J=8.9 Hz, 2×Ar—H), 6.75 (d, 2H, J=8.9 Hz, 2×Ar—H).

$^{13}$C NMR (75 MHz, $CDCl_3$) δ 30.6 ($CH_2$), 34.5 ($CH_2$), 53.2 ($CH_3$), 56.1 (CH), 114.6 (CH=C), 114.9 ($CH_2$=C), 115.2 (CH—Ar), 138.7 (CH—Ar), 142.3(C—Ar), 151.8 (C—Ar).

Exact mass calcd. for $C_{16}H_{23}NO$ ($M^+$) 245.1779, found 254.1779

EXAMPLE 11

Synthesis of Cycloheptene (15)

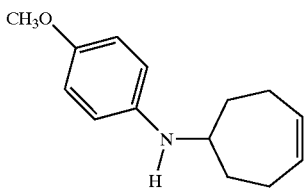

Diene (14) (200 mg, 0.81 mmol) was added to degassed dichloromethane (60 ml) and Grubbs' catalyst (65 mg, 0.08 mmol) was added. The reaction mixture was stirred at room temperature over night. Following evaporation of solvent and gradient elution (hexane to $CH_2Cl_2$) the cycloheptene (15) was obtained as a yellow oil. (101 mg, 57%)

$^1$H NMR (200 MHz, $CDCl_3$) δ 1.38 (m, 2H, $CH_2$), 2.05 (m, 4H, 2×$CH_2$), 2.23 (m, 2H, $CH_2$), 3.45 (oct, 1H, J=3.8 Hz, CH), 3.75 (s, 3H, $CH_3$), 5.79 (m, 2H, CH=CH), 6.57 (d, 2H, J=9.0 Hz, 2×Ar—H), 6.78 (d, 2H, J=9.0 Hz, 2×Ar—H).

$^{13}$C NMR (75 MHz, $CDCl_3$) δ 24.6 ($CH_2$), 33.3 ($CH_2$), 55.7 ($CH_3$), 56.2 (CH), 114.7 (C=C), 114.8 (CH—Ar), 131.6 (CH—Ar), 141.1 (C—Ar), 151.7 (C—Ar).

Exact mass calcd. for $C_{14}H_{20}NO$ (M+H) 218.1544, found 218.1553

EXAMPLE 12

Synthesis of Bicyclic (16)

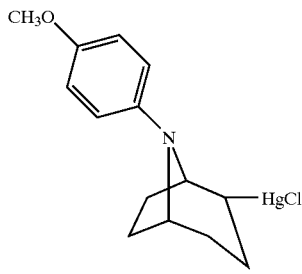

Mercuric acetate (37 mg, 0.115 mmol) was added to a solution of cycloheptene (15) (29 mg, 0.115 mmol) in dry dichloromethane (12 ml). The resulting mixture was stirred at room temperature overnight. After quenching with saturated aqueous sodium chloride (5 ml) and stirring for half an hour, the organic layer was separated and dried over anhydrous magnesium sulfate and concentrated. Gradient elution (hexane to $CH_2Cl_2$) gave the bicyclic (16) as a white solid (29 mg, 48%).

$^1$H NMR (200 MHz, $CDCl_3$) δ 1.25 (m, 1H, C̲H—H), 1.60–2.20 (m, 6H, $CH_2$), 2.40 (dq, 1H, J=1.4, 0.7 Hz, C H̲—H), 3.35 (dd, 1H,J=3.8, 9.0 Hz, CH—Hg), 3.75 (s, 3H, $CH_3$), 4.02 (bs, 1H, CHN), 4.38 (bs, 1H, CHN), 6.74 (bs, 2H, Ar—H), 6.85 (d, 2H, J=9.0 Hz, Ar—H).

$^{13}$C NMR (75 MHz, $CDCl_3$) δ 25.5 ($CH_2$), 28.5 ($CH_2$), 29.9 (CH 2), 30.6($CH_2$), 55.3($CH_3$), 55.7(CH), 55.9(CH), 59.2(CH), 115.2(CH—Ar), 116.3(CH—Ar), 139.9(C—Ar), 151.5(C—Ar).

M/z Electrospray calcd. for $C_{14}H_{20}NO$ ($M^+$) 452.3486, found 450.2, 451.2, 452.2, 454.2, 455.2, 456.2

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Crimmins, M. T. and King, B. W., *J. Org. Chem.*, 1996, 61, 4192–4193.

Evans, D. A., Ennis, M. D. and Mathre, D. J., *J. Am. Chem. Soc*, 1982, 104, 1737–1739.

Grubbs, R. H. and Chang, S., *Tetrahedron*, 1998, 54, 4413–4450.

Kobayashi, S., Fujishita, Y., Mukaiyuma, T., *Chemistry Lett.*, 1989, 2069–2072.

Kobayashi, S., Horibe, M., *J. Am. Chem. Soc.*, 1994, 116, 9805–9806. March, J. in *Advanced Organic Chemistry*, Third Ed., John Wiley & Sons Inc., 1985. Chapter 10: Aliphatic Nucleophilic Substitution p 255–447 and Chapter 16: Addition to Carbon Hetero Multiple Bonds p 780–873.

Mikami, K., Matsukawa, S., *J. Am. Chem. Soc.*, 1993, 15, 7039–7040.

Nagao, Y., Kumagai, T., Nagase, Y., Tamai, S., Inoue, Y. and Shiro, M., *J. Org. Chem.* 1992, 57, 4232–4237.

Oppolzer, W., Blagg, J., Rodriguez, I. and Walther, E., *J. Am. Chem. Soc*, 1990, 112, 2767–2772.

Perlmutter, P. Curr. Med. Chem. 1996, 3, 139.

Perlmutter, P. *Topics in Current Chemistry*, 1997, 190, 87–101

Schuster, M.; Blechert, S. *Angew. Chem. Int. Ed. Eng.* 1997, 36, 2037–2056.

Schwab P.; Grubbs R. H.; Ziller J. W. *J. Amer. Chem. Soc.* 1996, 118, 100–110.

Tait, R. M., *Anal. Biochem.* 1992, 203, 310–316.

Yamada, Y. M. A., Shibasaki, M. *Tetrahedron Lett.* 1998, 39, 5561–5564.

What is claimed is:

1. A method of synthesis of a bicyclic or polycyclic compound of formula I or formula II

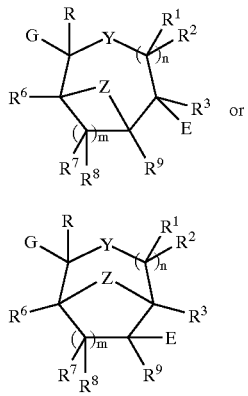

in which:

E represents an electrophile;

each of R, $R^1$, $R^2$, $R^3$, $R^6$, $R^7$, $R^8$ and $R^9$ independently represents hydrogen, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, allcylthio, benzylthio and acylthio, each of which may optionally be substituted, and wherein any two or more of R, $R^1$–$R^3$ and $R^6$–$R^9$ form an optionally substituted alkyl, alkenyl or alkynyl chain, which chain may also optionally include one or more O, N or S atoms therein;

Y represents $C(R^{12})R^{13}$, O, $NR^{14}$, or S, wherein $R^{12}$, $R^{13}$ and $R^{14}$ each independently have the same definition as R;

G represents W or X;

W represents an electron withdrawing group;

X is H;

Z represents O, $NR^{15}$, S or $CR^{16}W'$, where $R^{15}$ and $R^{16}$ each have the same definition as R, and W' has the same definition as W; and each of n and m represents an integer from 0 to 100; and the method comprises the steps of (a) treating a compound of formula III;

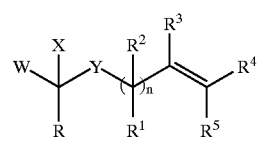

in which R, $R^1$–$R^3$, W, X and Y are as defined above for the compounds of formulae I and II, and $R^4$ and $R^5$ each independently have the same definition as R with base to form the corresponding enolate;

(b) subjecting a compound of formula W to nucleophilic addition by the enolate form of compound III;

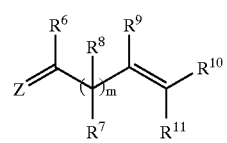

in which $R^6$–$R^{11}$ and Z are as defined above for the compounds of formulae I and II, and $R^{10}$ and $R^{11}$ each independently have the same definition as R;

(c) subjecting the product of step (b) to ring closing metathesis; and (d) subjecting the product of step (c) to stereoselective ring closure by reaction with a reagent selected from the group consisting of $HgCl_2$, $Hg(OCOR)_2$, $Br_2$, $Cl_2$, $I_2$, $RCO_3H$, $ArCO_3H$, and PhSeBr.

2. The method as claimed in claim 1, wherein the compound of formula I or formula II is a tropane alkaloid.

3. The method as claimed in claim 1 wherein E is selected from the group consisting of H, hydroxy, alkoxy, acyl, acyloxy, alkylsulphonyloxy, arylsulphenyloxy, hetercyclyloxy, carboalkoxy, carboaryloxy, alkylthio, benzylthio, acylthio, cyano, halo, aryloxy, benzyloxy, haloalkoxy, haloalkenyloxy, haloaryloxy, acids or esters of phosphorous or sulphur, and metal salts.

4. The method as claimed in claim 3, wherein each of n and m represents an integer from 0 to 25.

5. The method as claimed in claim 1 wherein W contains a chiral auxiliary.

6. The method as claimed in claim 5, wherein the chiral auxiliary is selected from the group consisting of Oppolzer's sultam, Evan's auxiliary and Nagao's auxiliary

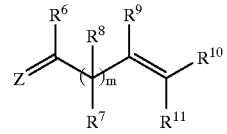

7. The method as claimed in claim 1 wherein either (1) the compound of formula III or the compound of formula IV is chiral or (2) both the compound of formula III and the compound of formula IV are chiral.

8. The method as claimed claim 1 wherein an enantiomerically-enriched additive system is used in step (b) to promote stereoselective coupling of the compounds of formulae III and IV.

9. The method as claimed in claim 8, wherein the additive system includes a catalyst or a promoter.

10. The method as claimed in claim 8, wherein the additive is selected from the group consisting of Sn (II) salts in combination with chiral, non-racemic diamine ligands, chiral, non-racemic Binol metal complexes, and chiral, non-racemic metal complexes of semicorrins.

11. A method according to claim 1 wherein Z represents $NR^{15}$.

12. A method according to claim 1 wherein Y represents $C(R^{12})R^{13}$.

13. A method according to claim 1 wherein Z=0.

14. A method of synthesis of a bicyclic or polycyclic compound of formula I or formula II

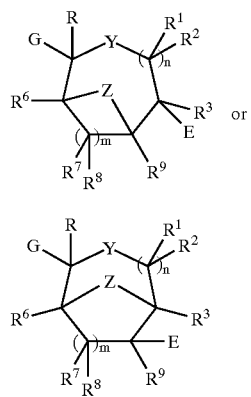

in which:
E represents an electrophile;
each of R, $R^1$, $R^2$, $R^3$, $R^6$, $R^7$, $R^8$ and $R^9$ independently represents hydrogen, alkyl, alkenyl, alkynyl, aryl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio and acylthio, each of which may optionally be substituted, and wherein any two or more of R, $R^1$–$R^3$ and $R^6$–$R^9$ may form an optionally substituted alkyl, alkenyl or alkynyl chain, which chain may also optionally include one or more O, N or S atoms therein;
Y represents $C(R^{12})R^{13}$, O, $NR^{14}$ or S, wherein $R^{12}$, $R^{13}$ and $R^{14}$ each independently have the same definition as R;
G represents X;
W is a halogen;
X has the same definition as R;
Z represents O, $NR^{15}$, S or $CR^{16}W'$, where $R^{15}$ and $R^{16}$ each have the same definition as R, and W' has the same definition as W; and each of n and m represents an integer from 0 to 100; and the method comprises the steps of
(a) subjecting a compound of formula III;

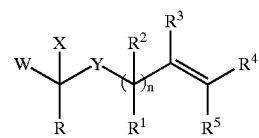

in which R, $R^1$–$R^3$, W, X and Y are as defined above for the compounds of formulae I and II, and $R^4$ and $R^5$ each independently have the same definition as R to halogen metal exchange at the carbon atom to which W is attached in the compound of Formula III to form the corresponding organometallic reagent;
(b) subjecting a compound of formula IV to nucleophilic addition by the organometallic reagent formed in step (a);

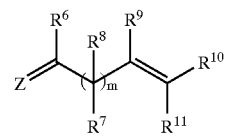

in which $R^6$–$R^{11}$ and Z are as defined above for the compounds of formulae I and H, and $R^{10}$ and $R^{11}$ each independently have the same definition as R;
(c) subjecting the product of step (b) to ring closing metathesis; and
(d) subjecting the product of step (c) to stereoselective ring closure by reaction with a reagent selected from the group consisting of $HgCl^2$, $Hg(OCOR)_2$, $Br_2$, $Cl_2$, $I_2$, $RCO_3H$, $ArCO_3H$, and PhSeBr.

15. The method as claimed in claim 14, wherein the compound of formula I or formula II is a tropane alkaloid.

16. The method as claimed in claim 14 wherein E is selected from the group consisting of H, hydroxy, alkoxy, acyl, acyloxy, alkylsulphonyloxy, arylsulphenyloxy, hetercyclyloxy, carboalkoxy, carboaryloxy, alkylthio, benzylthio, acylthio, cyano, halo, aryloxy, benzyloxy, haloalkoxy, haloalkenyloxy, haloaryloxy, acids or esters of phosphorous or sulphur, and metal salts.

17. The method as claimed in claim 14, wherein each of n and m represents an integer from 0 to 25.

18. The method as claimed in claim 14, wherein either (1) the compound of formula III or the compound of formula W is chiral or (2) both the compound of formula III and the compound of formula IV are chiral.

19. The method as claimed in claim 14, wherein an enantiomerically-enriched additive system is used in step (b) to promote stereoselective coupling of the compounds of formulae III and IV.

20. The method as claimed in claim 19, wherein the additive system includes a catalyst or a promoter.

21. The method as claimed in claim 19, wherein the additive is selected from the group consisting of Sn (II) salts in combination with chiral, non-racemic diamine ligands, chiral, non-racemic Binol metal complexes, and chiral, non-racemic metal complexes of sermcorrins.

22. A method according to claim 1, wherein the reagent used in step (d) is HgCl2 or Hg(OAc)2.

23. A method according to claim 14, wherein the reagent used in step (d) is HgCl2 or Hg(OAc)2.

* * * * *